United States Patent [19]

Finney et al.

[11] Patent Number: 5,011,586

[45] Date of Patent: Apr. 30, 1991

[54] CONSTRAINED UNIFORM FIELD GEL ELECTROPHORESIS

[75] Inventors: John D. Finney, Boston; Michael J. Finney, Arlington, both of Mass.

[73] Assignee: MJ Research, Inc., Cambridge, Mass.

[21] Appl. No.: 289,966

[22] Filed: Dec. 23, 1988

Related U.S. Application Data

[63] Continuation-in-part of Ser. No. 231,821, Aug. 12, 1988.

[51] Int. Cl.$^5$ ............... G01N 27/26; B01D 57/02
[52] U.S. Cl. ............... 204/299 R; 204/182.8
[58] Field of Search ............ 204/182.8, 182.9, 180.1, 204/299 R

[56] References Cited

U.S. PATENT DOCUMENTS

| | | | |
|---|---|---|---|
| 4,148,703 | 4/1979 | Trop et al. | 204/180 G |
| 4,473,452 | 9/1984 | Cantor et al. | 204/180 G |
| 4,614,576 | 9/1986 | Goldstein | 204/299 R |
| 4,693,804 | 9/1987 | Serwer | 204/182.1 |
| 4,695,548 | 9/1987 | Cantor et al. | 435/179 |
| 4,737,251 | 4/1988 | Carle et al. | 204/182.8 |
| 4,740,283 | 4/1988 | Laas et al. | 204/182.8 |

OTHER PUBLICATIONS

Chu et al., "Separation of Large DNA Molecules by Contour-Clamped Homogeneous Electric Fields," Science, vol. 234, p. 1582, 1986.
Beckman, "Geneline, Transverse Alternating Field Electrophoresis System," Beckman Instruments, Inc. 1987, pp. 1-7.

Primary Examiner—John F. Niebling
Assistant Examiner—John S. Starsiak, Jr.
Attorney, Agent, or Firm—Fish and Richardson

[57] ABSTRACT

A gel electrophoresis apparatus for separating DNA molecules of high molecular weight having means for generating at least two electric fields oriented transversely to each other, and a gel box, shaped, and contoured to simultaneously form both the electric fields into uniform electric fields.

17 Claims, 12 Drawing Sheets

TWO FIELD X-BOX
NO BAFFLES

Field A
Strength and Direction

Field B
Strength and Direction

TWO FIELD X-BOX NO BAFFLES

| | A | B | C | D | E | F | G | H | I | J | K | L | M | N | O | P | Q | R |
|---|---|---|---|---|---|---|---|---|---|---|---|---|---|---|---|---|---|---|
| 1 | | | 0 | 0.5 | 1 | 1.5 | 2 | 2.5 | 3 | 3.5 | 4 | 4.5 | 5 | 5.5 | 6 | 6.5 | 7 | 7.5 |
| 2 | | | | | | | | | | | | | | | | | | |
| 3 | 4 | | | | | | | | | | | | | | | | | |
| 4 | 4.5 | | | | | | | | | | | | | 6.4 | | | | |
| 5 | 5 | | | | | | | | | | | | | 6.3 | | | | |
| 6 | 5.5 | | | 4.2 | 4 | 3.9 | 4 | 5.1 | 5.3 | 5.7 | 5.8 | 5.8 | 6 | 6.2 | 6.4 | | | |
| 7 | 6 | | 3.3 | 3.7 | 3.8 | 3.8 | 3.9 | 5 | 5.3 | 5.5 | 5.7 | 5.8 | 6 | 6 | 6.2 | 6.5 | | |
| 8 | 6.5 | | 3.2 | 3.2 | 3.8 | 3.7 | 4 | 4.9 | 5.1 | 5.5 | 5.6 | 5.4 | 6 | 5.9 | 5.9 | 5.8 | | |
| 9 | 7 | | 3 | 3 | 3.9 | 3.9 | 4 | 4.8 | 5 | 5.3 | 5.5 | 5.4 | 5.8 | 5.6 | 5.7 | 5.2 | | |
| 10 | 7.5 | | 3.3 | 3.5 | 4 | 3.9 | 4.1 | 4.8 | 4.9 | 5.1 | 5.3 | 5.3 | 5.5 | 5.3 | 5.2 | 4.7 | 4.7 | |
| 11 | 8 | | 3.9 | 4.2 | 4 | 4.3 | 5 | 4.9 | 4.9 | 5 | 5.1 | 5 | 5.3 | 5 | 5 | 5.2 | 4.2 | |
| 12 | 8.5 | | 4.5 | 4.3 | 4.5 | 4.5 | 5.1 | 5 | 5 | 5 | 5 | 5 | 5 | 5 | 4.8 | 4.7 | 4.1 | |
| 13 | 9 | | | 4.8 | 4.7 | 4.7 | 5.2 | 5 | 5 | 4.9 | 4.9 | 4.9 | 4.9 | 4.7 | 4.3 | 4.4 | 3.4 | 3.3 |
| 14 | 9.5 | | | 5.3 | 5 | 5 | 5.4 | 5.1 | 5.2 | 4.9 | 4.9 | 4.8 | 4.7 | 4.5 | 4.2 | 3.9 | 3.4 | |
| 15 | 10 | | | | 5.1 | 5 | 5.5 | 5.3 | 5.3 | 4.8 | 4.8 | 4.7 | 4.7 | 4.5 | 4 | 3.8 | 3.4 | |
| 16 | 10.5 | | | | | 5 | 5.5 | 5.4 | 5.4 | 5 | 4.7 | 4.7 | 4.6 | 4.4 | 4.2 | 3.7 | | |
| 17 | 11 | | | | | 5 | 5.6 | 5.5 | 5.4 | 5.1 | 4.8 | 4.7 | 4.6 | 4.4 | 4 | 3.7 | | |
| 18 | 11.5 | | | | | 5.2 | 5.6 | 5.6 | 5.4 | 5.2 | 4.9 | 4.8 | 4.5 | 4.4 | | | | |
| 19 | 12 | | | | | 5.2 | 5.6 | 5.7 | 5.6 | | | 5 | | | | | | |

FIG.5E

Grid Layout for CUFE Field Strength Measurements

TWO FIELD X-BOX
NO BAFFLES
FIG.5B
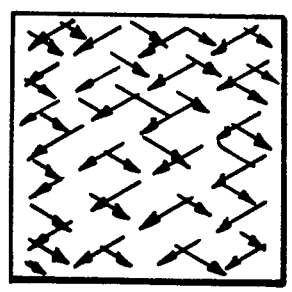
Field A superimposed on field B
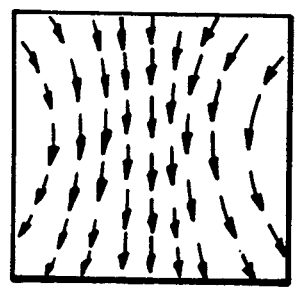
Vector sum of fields A and B
FIG.5C

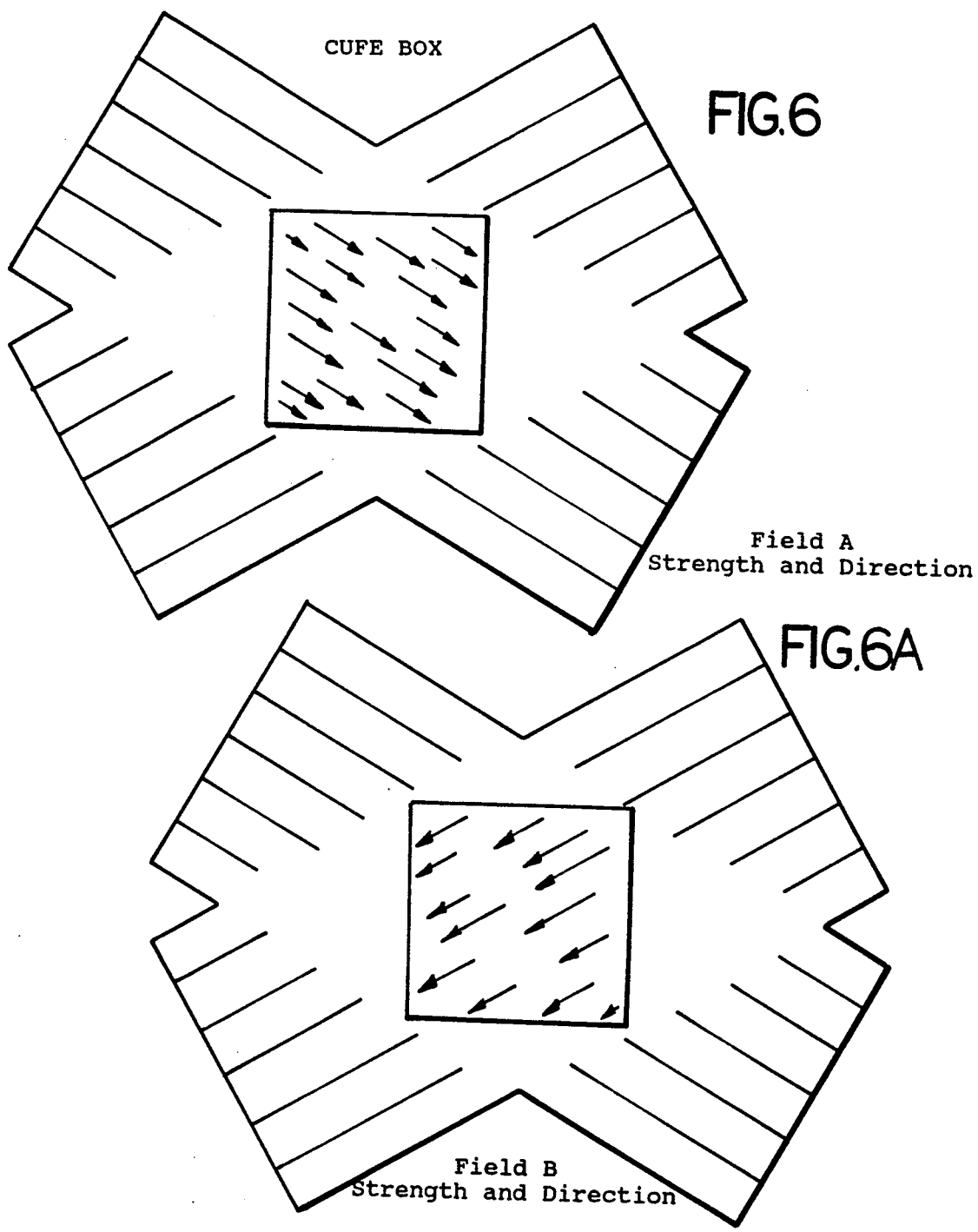

CUFE BOX

Vector sum of fields
A and B

FIG.6C

CuFe FIELD STRENGTH

|   | A | B | C | D | E | F | G | H | I | J | K | L | M | N | O | P | Q | R |
|---|---|---|---|---|---|---|---|---|---|---|---|---|---|---|---|---|---|---|
|   |   |   | 0 | 0.5 | 1 | 1.5 | 2 | 2.5 | 3 | 3.5 | 4 | 4.5 | 5 | 5.5 | 6 | 6.5 | 7 | 7.5 |
| 1 |   |   |   |   |   |   |   |   |   |   |   |   |   |   |   |   |   |   |
| 2 |   |   |   |   |   |   |   |   |   |   |   |   |   |   |   |   |   |   |
| 3 | 4 |   |   |   |   |   |   |   |   |   |   |   |   |   |   |   |   |   |
| 4 | 4.5 |   |   |   |   |   |   |   |   |   |   |   |   |   |   |   |   |   |
| 5 | 5 |   |   |   |   |   |   |   |   |   |   |   | 6 | 6.1 |   |   |   |   |
| 6 | 5.5 |   |   |   |   |   |   |   |   |   |   |   |   |   |   |   |   |   |
| 7 | 6 |   |   |   |   |   |   |   | 6 | 5.9 | 5.8 | 5.8 | 5.8 | 6.2 | 6.1 |   |   |   |
| 8 | 6.5 |   |   | 5.9 | 5.8 | 5.8 | 5.8 | 5.9 | 5.9 | 5.9 | 5.8 | 5.8 | 6 | 6.1 | 5.9 | 6.2 |   |   |
| 9 |   |   | 5.0 | 5.9 | 5.8 | 5.8 | 5.8 | 5.9 | 5.8 | 5.9 | 5.8 | 5.8 | 6 | 6.2 | 6 |   |   |   |
| 10 | 7 |   | 6.1 | 5.8 | 5.9 | 5.8 | 5.8 | 5.9 | 5.8 | 5.9 | 5.9 | 5.8 | 6 | 6.1 | 5.9 |   |   |   |
| 11 | 7.5 |   | 6.1 | 5.8 | 5.9 | 5.8 | 5.8 | 5.9 | 6.1 | 5.9 | 6 | 5.8 | 6 | 6 | 5.8 | 6 |   |   |
| 12 | 8 |   | 5.9 | 5.8 | 5.8 | 5.8 | 5.9 | 5.9 | 6.1 | 5.9 | 5.9 | 5.9 | 5.9 | 5.9 | 6 | 6 | 5.9 |   |
| 13 | 8.5 |   |   |   | 5.8 | 5.8 | 5.9 | 5.9 | 6.1 | 5.9 | 5.9 | 5.9 | 5.8 | 5.8 | 6 | 6 | 5.9 |   |
| 14 | 9 |   |   | 5.8 | 5.8 | 5.8 | 5.8 | 6 | 6.1 | 6 | 6 | 5.9 | 5.8 | 5.9 | 6 | 5.9 | 5.8 | 5.8 |
| 15 | 9.5 |   |   |   |   | 5.9 | 5.9 | 5.9 | 6.1 | 6.1 | 5.9 | 5.8 | 5.9 | 5.8 | 6 | 6.1 | 6 | 6 |
| 16 | 10 |   |   |   |   |   | 5.8 | 6 | 6.1 | 6.1 | 6 | 5.8 | 6 | 5.8 | 6 | 6.1 | 6 | 6.1 |
| 17 | 10.5 |   |   |   |   |   | 5.9 | 5.9 | 6.2 | 6.1 | 6.1 | 5.8 | 6 | 5.8 | 6 | 6.1 | 5.8 | 5.9 |
| 18 | 11 |   |   |   |   |   | 5.8 | 6.1 | 6 | 6.1 | 6 | 5.8 | 6 | 5.8 | 6 | 6.1 | 6 |   |
| 19 | 11.5 |   |   |   |   |   | 5.9 | 6.1 | 6.2 | 6.2 |   |   | 6 |   | 6.1 |   |   |   |
|   | 12 |   |   |   |   |   | 6 |   |   |   |   |   |   |   |   |   |   |   |

CONSTRAINED UNIFORM FIELD GEL ELECTROPHORESIS

BACKGROUND OF THE INVENTION

This application is a continuation-in-part of Finney et al., U.S. Ser. No. 231,821, filed Aug. 12, 1988, entitled CONSTRAINED UNIFORM FIELD GEL ELECTROPHORESIS.

This invention concerns apparatus for gel electrophoresis of high molecular weight DNA.

It is known that an electric field can be used to move DNA molecules through semi-solid gels in order to separate the molecules on the basis of size. Small molecules move faster than large ones because they encounter less resistance from the gel matrix. Molecules up to about 30,000 bases in length can be separated in this way; larger molecules (up to many million bases in length) all move at about the same rate, and thus are more difficult to separate.

Recently, a few systems have emerged that exhibit a reduction in the limitations experienced during standard electrophoresis. These systems depend on periodic changes in the direction of the electric field in the gel. For example, Cantor et al. (U.S. Pat. Nos. 4,473,452 and 4,695,548) describe a system in which generally non-uniform electric fields change direction in the plane of the gel. While the mechanism by which this electrophoresis method operates to move large DNA molecules is not entirely understood, Cantor et al. propose that the application of alternating fields causes a coiled DNA molecule to be squeezed into the gel matrix by orientating itself first along the general direction of one of the fields and then along the general direction of the other, and so on. Moreover, they believe that by using gradient fields, rather than uniform fields, a shearing effect is produced that helps stretch the DNA molecule in a desired direction. Carle et al. (U.S. Pat. No. 4,737,251) describe a method for field inversion electrophoresis. In this method, the electric field is changed in direction by 180°. Net migration is achieved by using a longer time or higher voltage in one direction than in the other direction. Chu et al. (234 Science 1582, 1986) describe a method of electrophoresis termed "contour clamped" or "homogenous electric field" electrophoresis. This method of electrophoresis depends on a complex network of diodes and resistors to fix the electric potential at a number of points around the gel, and thus fix the electric field in the gel. This method can also be used for electrophoresis in non-uniform fields. Laas et al. (U.S. Pat. No. 4,740,283) and a 1987 Beckman Instrument advertisement entitled GENELINE TM describe a pulse field gradient gel electrophoresis apparatus having electrode arrays oriented to provide three dimensional fields across the face of the gel. Serwer (U.S. Pat. No. 4,693,804) describes an apparatus for conducting electrophoresis in two dimensions without need to move a gel after electrophoresis in a first dimension. Barriers are provided to limit an electric field to a rectangular shape and prevent passage of electricity. After electrophoresis in a first dimension these barriers are removed and new barriers erected to form a new electric field in a rectangular shape oriented at 90° to the first.

SUMMARY OF THE INVENTION

This invention features an electrophoresis apparatus and method which provide good resolution of high molecular weight DNA molecules at low cost. Generally, the electrophoresis chamber of the apparatus is shaped to constrain two transversely applied electric fields such that high-molecular weight DNA is resolved in straight gel lanes by uniform electric fields. This invention can be used at a high power rating with any thickness of gel and any conductivity of buffer that is normally used for gel electrophoresis, including gels useful for preparative and high sensitivity work. Buffers of high conductivity are especially preferred for resolution of high molecular weight DNA. Power consumption may also be maintained at a low enough level to require only inexpensive power supplies that are commonly used for DNA gel electrophoresis. The gel may be sized as required, the limitation being physical, rather than electrical.

Thus, the invention features, in a first aspect, gel electrophoresis apparatus for separating DNA molecules of high molecular weight having means for generating first and second electric fields, the fields being oriented transversely to each other, and a gel box shaped and contoured to simultaneously form both the electric fields into generally uniform electric fields.

By "uniform electric field" is meant that the electric field strength (in volts/cm) generated in the gel box varies by less than 20% from an average value in the gel box, preferably less than 10% and even more preferably less than 5%, particularly in the area of the gel box in which a DNA sample is placed and electrophoresed. By "simultaneously" is meant that the gel box is shaped and contoured to form both of the electric fields into uniform electric fields without need for the gel box to be altered in its shape or contouring when the means is switched to generate either electric field.

In preferred embodiments, the means includes at least four electrodes positioned near the outer perimeter of the box which is defined by a wall forming the shape of the box. The outer perimeter is shaped to accept a gel and buffer, the perimeter having the shape of two rectangles placed on top of each other at an angle of between 90° and 135°, preferably the rectangles are identical in shape, and at least one corner of one rectangle coincides with a corner of the other rectangle, most preferably the rectangles coincide at two corners. The gel box includes at least one baffle means formed of electrically non-conducting material positioned and arranged to limit formation of a non-uniform electric field in the gel box. Generally, the baffle means is oriented along the overall direction of the first electric field, and is positioned and arranged to limit formation of a non uniform field in the second electric field; most preferably, the baffle means is a set of baffle elements and the apparatus has a plurality of these baffle elements, with at least one baffle element, but preferably all baffle elements, oriented along the overall direction of the first or second electric field to prevent formation of a non-uniform electric field in the other electric field. The baffle means is preferably in contact with the outer perimeter and base of the gel box, and has a height equal to that of the gel box. Most preferably, each baffle element is in contact with the outer perimeter of the gel box and extends along the direction of the first or second uniform electric field to the edge of the other uniform electric field. Each electrode is generally separated from all other electrodes of the same polarity by a baffle formed of electrically non-conducting material, the baffle preventing direct electric conduction between these electrodes through a medium in the gel box. In another preferred embodiment, the apparatus is suitable for use in DNA sequencing, having two plates and a baffle means positioned to sandwich a polyacrylamide gel.

In a second aspect, the invention features a method for separating DNA molecules of high molecular weight, including the steps of positioning the DNA molecules within a gel matrix; providing means for generating alternating transversely applied uniform electric fields, and positioning the gel matrix in a gel box sized, shaped, and contoured to simultaneously form two generally transverse uniform electric fields, and subjecting the gel matrix to these alternating electric fields.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

Figure 5:
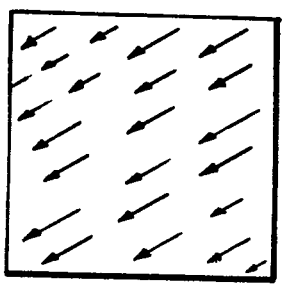
Figure 5A:
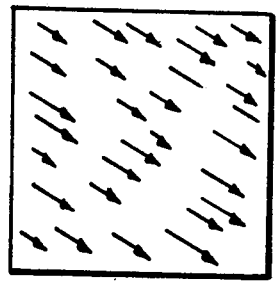
Figure 5D:
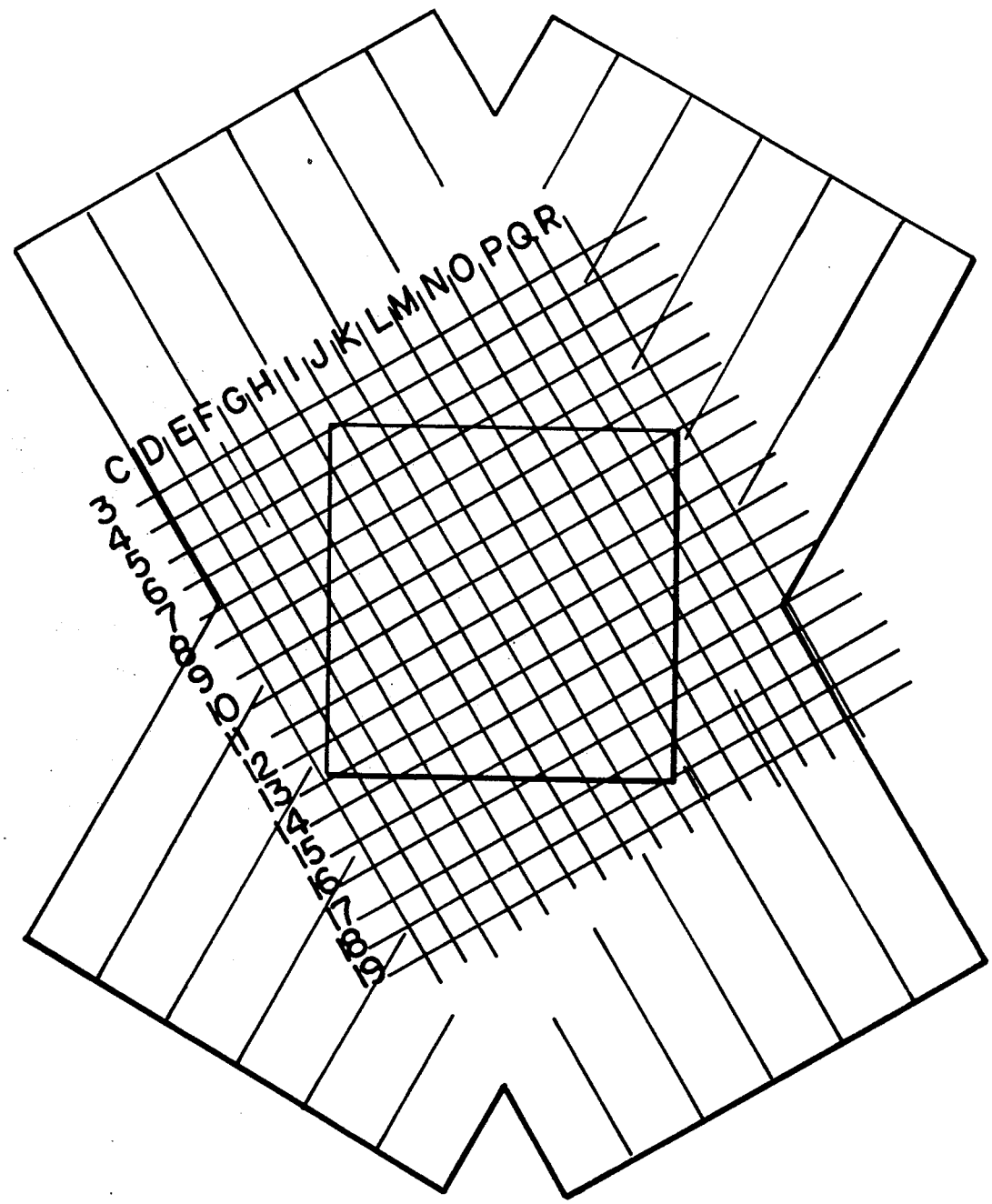
Figure 6B:
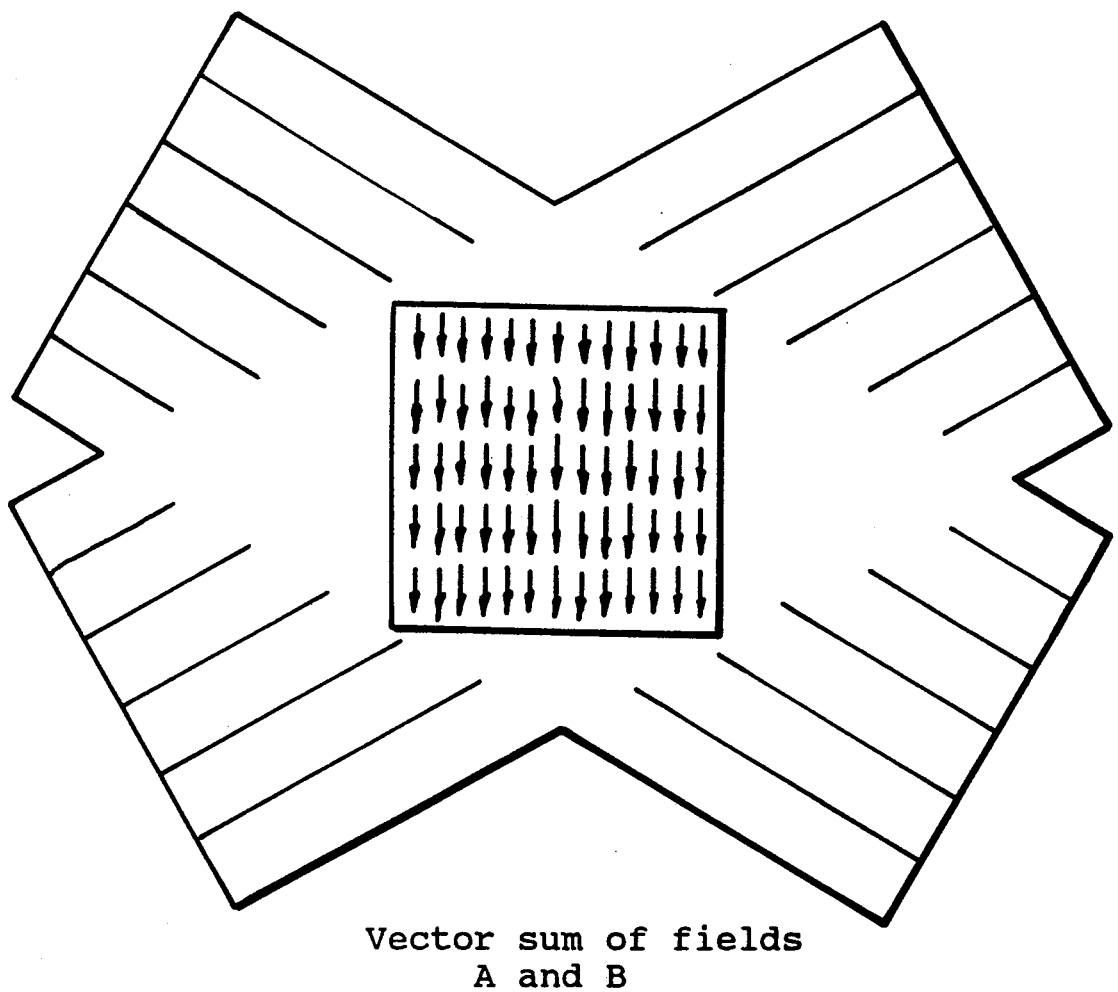

FIGS. 5, 5A, and 5B are top views of an electrophoresis cell without baffles showing field strength and direction during electrophoresis in a region of the cell, FIG. 5C shows the vector sum of these field strengths, FIG. 5D shows a grid layout used for measuring the field strength, and FIG. 5E shows numerical values of field strengths in V/cm in one electric field;

FIGS. 6 and 6A are top views of an electrophoresis cell with baffles showing field strength and direction during electrophoresis in a region of the cell, FIG. 6B shows the vector sum of the field strengths, and FIG. 6C show numerical values of field strength in V/cm in one electric field.

Figure 7:
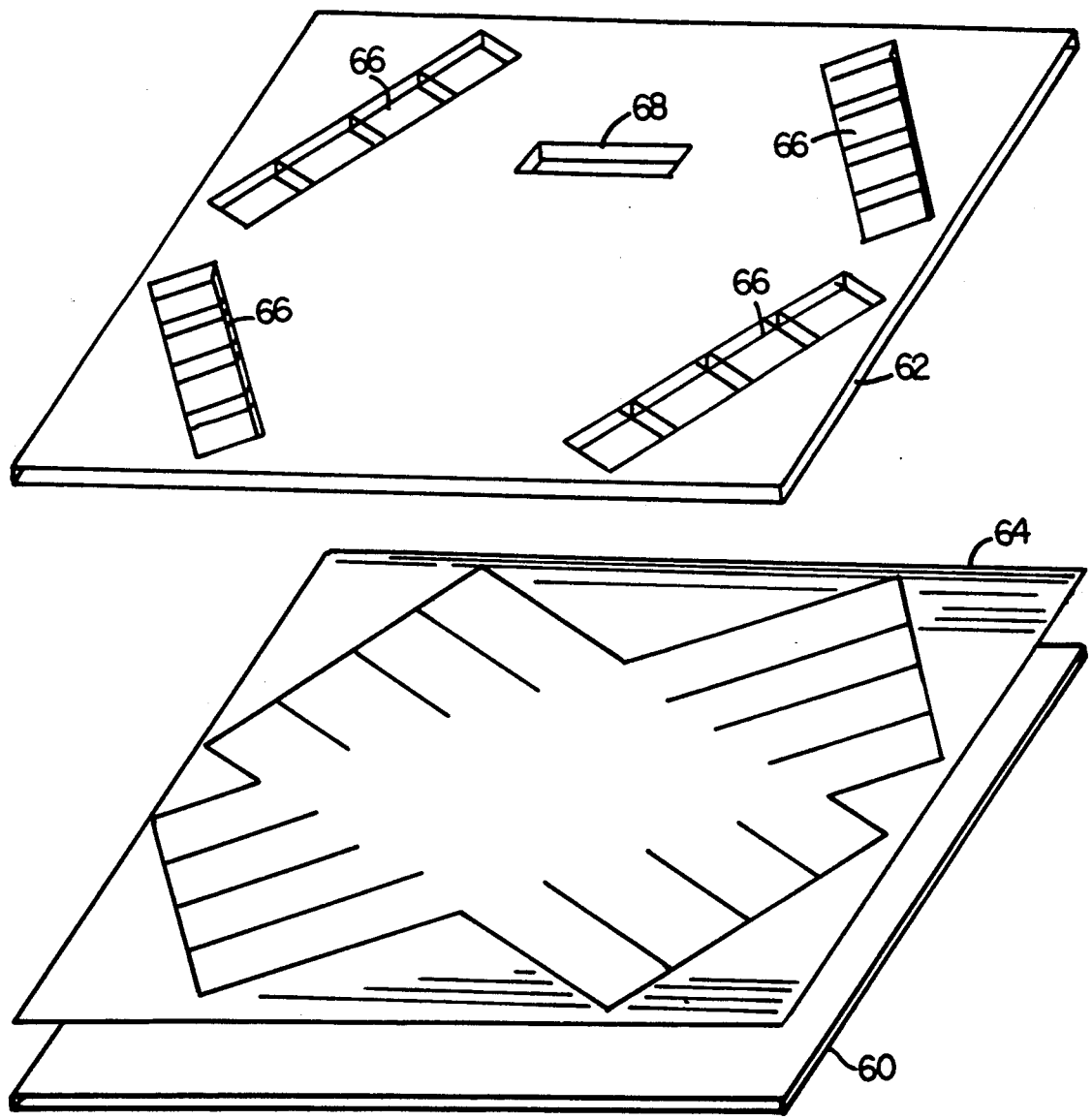

FIG. 7 is an isometric view of an electrophoresis cell suitable for use in DNA sequencing.

STRUCTURE

One example of an electrophoresis cell useful in this invention generally has an X-shape, and is termed an X-box. Two uniform electric fields which alternate at a 120° angle to each other are provided. Uniformity of fields is achieved by the shape of the electrophoresis cell of the invention.

Figure 1:
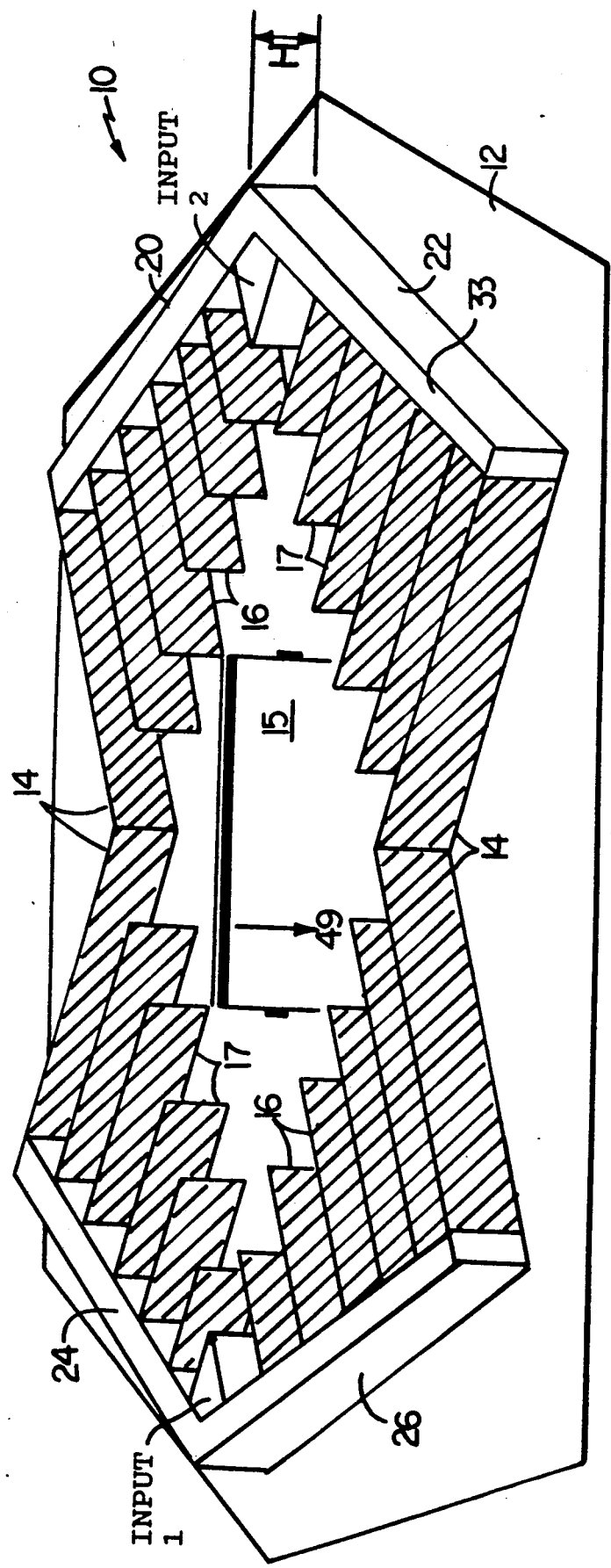
FIGS. 1 and 2 are an isometric view and a top view respectively of an electrophoresis cell of the invention.
Figure 2:
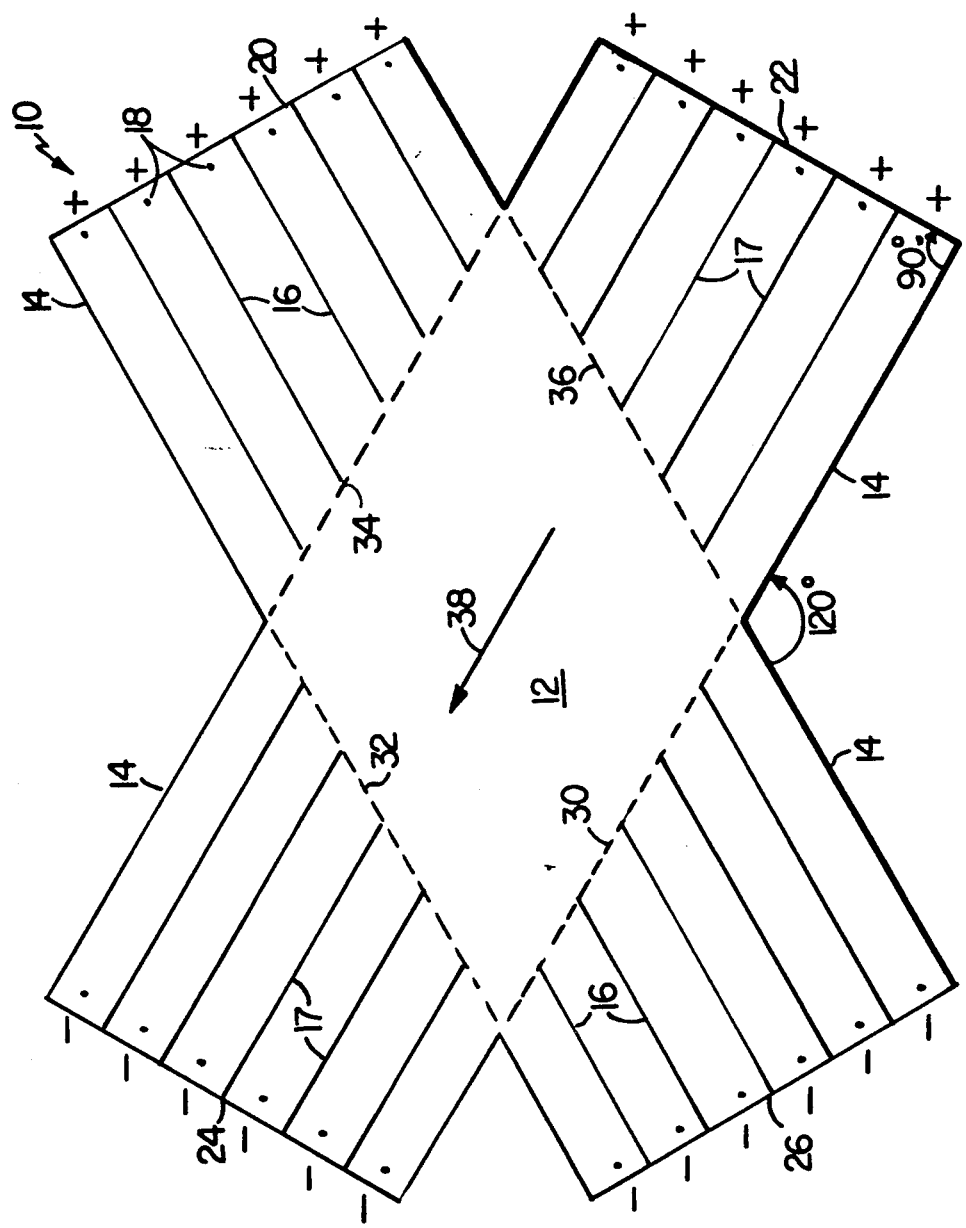

Referring to FIGS. 1 and 2, X box 10 has a flat base 12 of an electrically non-conducting material, such as acrylic plastic. Vertical walls 14 in combination with ends 20, 22, 24 and 26 define an outer perimeter, and with the base define a volume for containing a gel 15 and buffer. Baffle elements 16, 17 extend, respectively, from ends 20, 26 and ends 22, 24. The baffle elements, walls and ends are also all formed of electrically non-conductive material. The baffle elements are disposed generally perpendicular to the base and ends, and are joined thereto. The walls, ends and baffles are generally of the same height, H, e.g., approximately two to three centimeters, so that the box contains a gel and a sufficient volume of electrophoresis buffer to completely immerse the gel.

The basic shape of the cell is of two superimposed identical rectangles at 120° angles to each other, having a common center, and placed so that the ends of the rectangles form four sides of a twelve-sided structure. Each rectangle has a multiplicity of small electrode pairs 18, e.g., six are shown, placed along ends 20, 22, 24 and 26 to provide the required electrical potential (shown as "+" and "−") across the box. The nonconductive baffles 16, 17 are disposed between electrodes 18 along each end surface, parallel to the sides of their respective rectangles. The baffles extend from the ends 20, 22, 24 and 26 of their respective rectangles, to the edges of the area common to the two rectangles. This common area is in the shape of a diamond, indicated by dotted lines 30, 32, 34 and 36. Each baffle element is oriented parallel to the length of the rectangle in which it is contained, so that the baffle element has little effect on the uniformity of an electric field set up along the length of that rectangle Each baffle is positioned and arranged to limit the non-uniformity of an electric field along the length of the rectangle that does not contain that baffle element. Each element thus extends from the end of one rectangle to the nearest edge of the other rectangle. In addition, each electrode is separated from all other electrodes of the same polarity by a baffle element.

Figure 4:
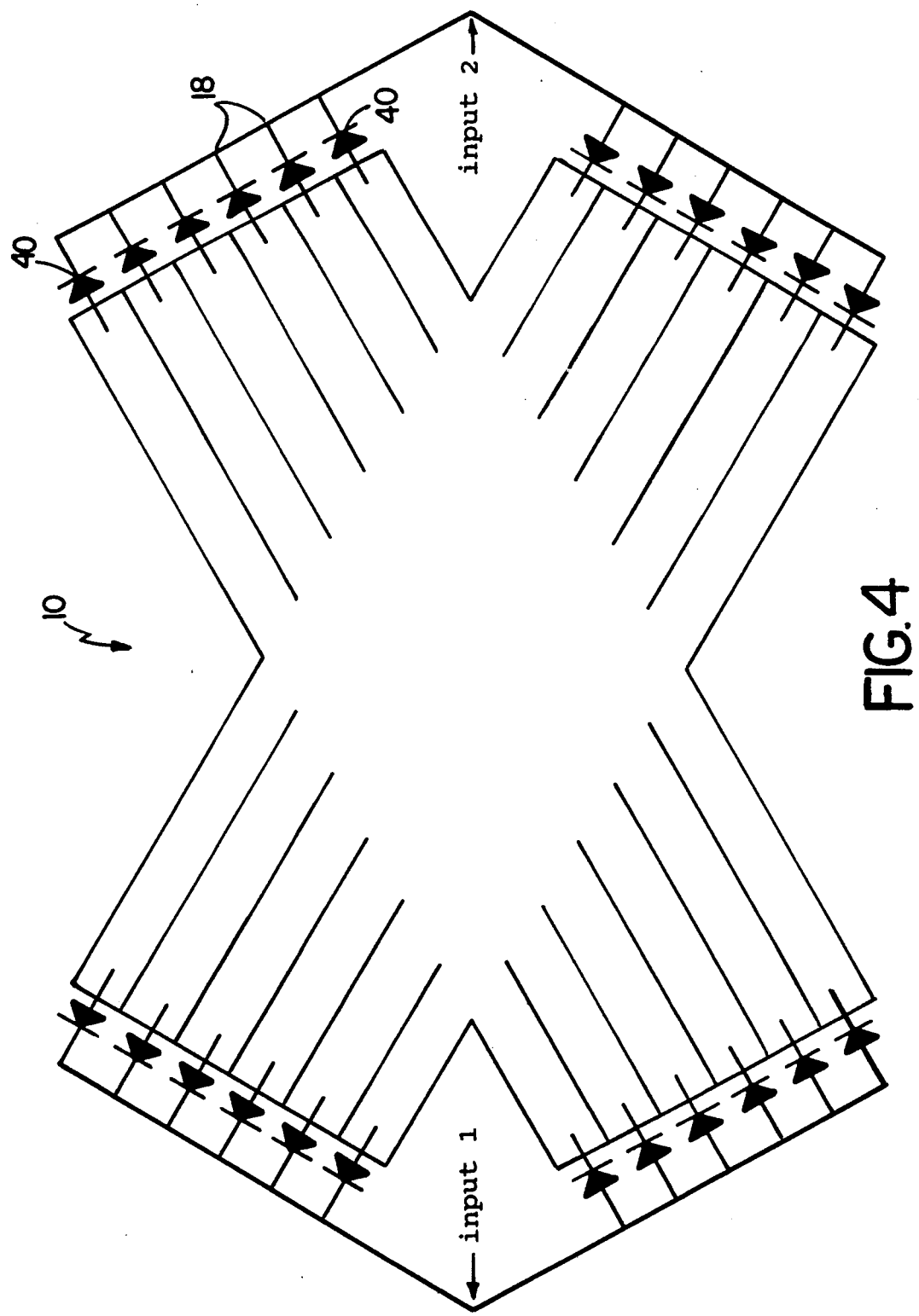
FIG. 4 is a schematic diagram of the wiring of an electrophoresis cell.

Referring to FIG. 4, gel box 10 is wired with each electrode 18 isolated to prevent current from flowing between electrodes that are in the off state. This is accomplished by connecting each electrode through a diode 40. This wiring plan has the additional advantage of allowing the gel box 55 to be connected with only two wires, labelled input 1 and input 2. When input 1 is positive and input 2 negative, current will flow through one of the rectangles; when the inputs are reversed, current will flow through the other. This simple arrangement allows the X box to be used with an inexpensive inverting controller such as a PPI-200 (MJ Research, Md.). Referring again to FIG. 1, these diodes are covered by a plastic material 33 to rescue the chances of inadvertant breakage.

Figure 3:
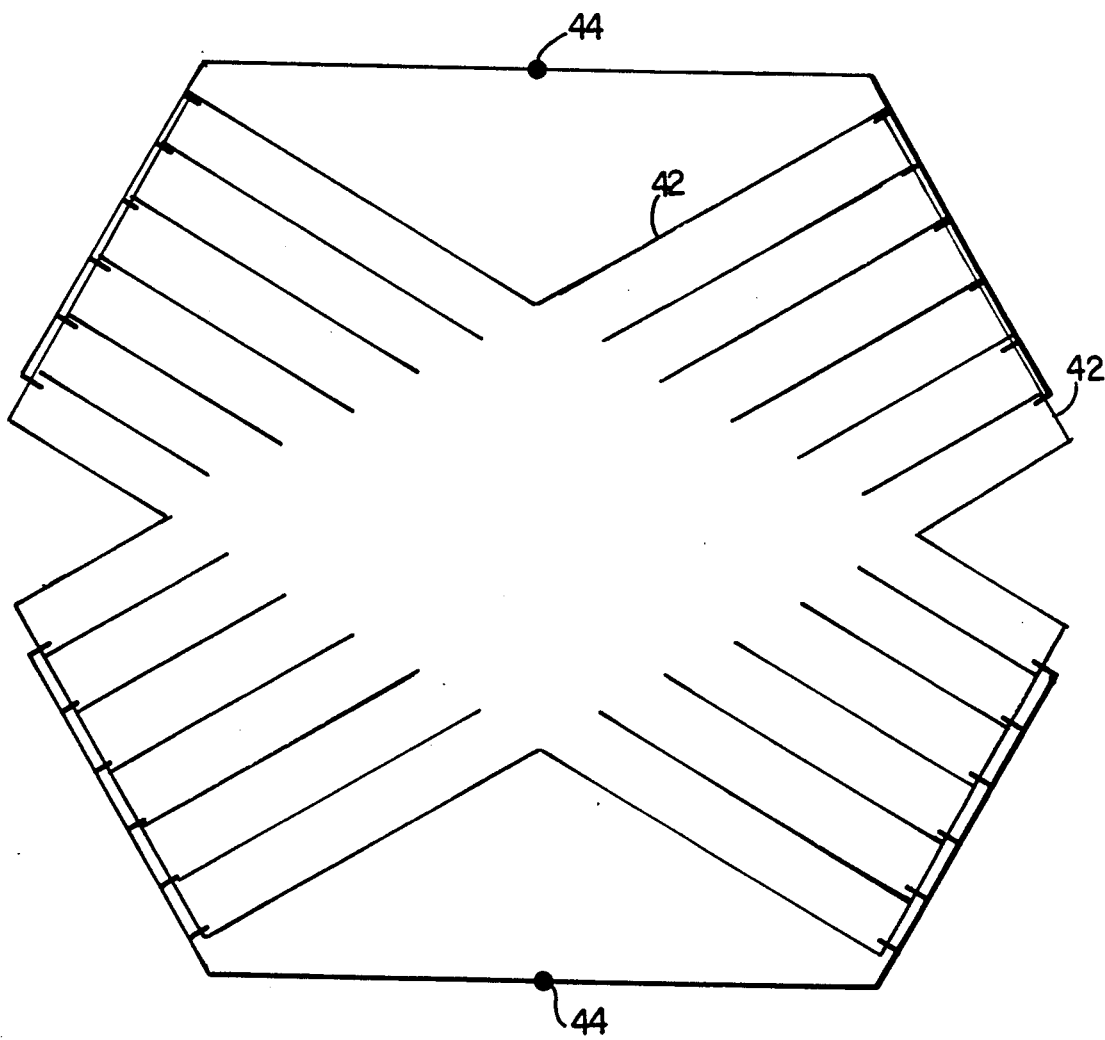
FIG. 3 is a diagrammatic representation showing recirculation ports in an electrophoresis cell.

To maintain temperature and pH uniformity of buffer in gel box 10, it is desirable to recirculate the buffer used for running a gel. The channels through which the buffer is recirculated are kept narrow so that very little current flows through them. By way of example only, a plan for buffer recirculation ports is shown in FIG. 3. Small (e.g., 1-2 mm diameter) channels 42 are milled into the base of box 10 before side walls 14 are attached. The sections of the channels outside box 10 are covered by a plastic strip adhesively connected to box 10, giving a system that is sealed everywhere except for two ports 44. Buffer is pumped from one port to the other. The advantage of this arrangement is that the greatest amount of recirculating flow occurs where it is needed most, i.e., in the regions of the longest baffles.

OPERATION

Referring to FIGS. 1 and 2, when an electric potential is applied between ends 22, 24 of one of the rectangles, an electric field 38 is set up across that rectangle. Baffles in that rectangle are oriented parallel to the direction of the field, and so do not affect the field. The baffles in the unenergized rectangle, however, are oriented at a 60° angle to the field, and so constrain the electric field to a generally rectangular shape. An electric field constrained to a generally rectangular shape is nearly uniform. Measurement of the field strength and direction in the area of a gel within an X box with or without baffles is shown in FIGS. 5-5E and 6-6C. These figures demonstrate that when baffles are provided the field strength is uniform to within 3.3% in the gel box the area of the gel, and without baffles may vary by as much as 50%. In FIGS. 5 and 5A and 6 and 6A field strength and direction is represented by the length of each line and by the arrow head for various positions within an X-box. Without baffles field strength varies greatly, with baffles it is of uniform size and direction. FIG. 5B demonstrates superimposition of field strength measurements in the two electric fields, and is summarized for each X box in FIGS. 5C and 6B, respectively. This is the overall field strength and direction experienced by DNA with a gel. For a box without baffles the field strength and direction is significantly distorted from a straight line, while for a box with baffles the field strength and direction is not distorted. FIG. 5D provides a grid for measuring electric field strength. The results of such measurements are provided in FIGS. 5E and 6C. The electric field strength in volts per centimeter is indicated. None of the measured field strengths vary by more than 3.3% from the average value for the entire gel when baffles are provided, but vary by more than 50% without the baffles. Thus, the electric field is uniform.

Referring to FIG. 1, a standard gel 15 is placed so that it rests on the base of a buffer-filled X-box 10, and the two rectangular fields energized alternately for equal periods of time (e.g., 10 to 60 sec.). DNA molecules migrating in the gel follow a zig-zag path with 120° resulting in a net migration that is straight, shown by arrow 49.

The principle of operator is independent of the conductivity of the buffer, the depth of the buffer in the box, and the size of the box; X-boxes can be easily scaled to any size.

OTHER EMBODIMENTS

Other embodiments are within the following claims. For example, a gel box of this invention and the method of its use can be adapted for use in DNA sequencing. A standard sequencing gel is made between two glass plates and incorporates 0.4 mm (or thinner) plastic spacers which fit between the plates to constrain the electric fields to be uniform. For example, referring to FIG. 7, electrophoresis is performed with the gel contained between two flat plates 60, 62 of an electrically non conducting material, such as glass. The two plates are held at a fixed distance apart, typically 1 mm or less, by a perimeter and baffle means 64 consisting of a thin layer of an electrically non conducting material such as plastic. The perimeter and baffle means is shaped to form an outer perimeter and baffle elements as described for an X-box. Electrophorersis is performed with the apparatus in a horizontal position. In this position, the lower plate may be of any size and shape provided that it is larger in every direction than the perimeter and baffle means. The upper plate covers all of the perimeter and baffle means except that it provides an access 66 to the gel at each end of both rectangles so that buffer chambers (not shown) containing buffer and an electrode can come into electrical contact with the gel. At least one buffer chamber and electrode is present at each end of each rectangle. The upper plate also contains a hole 68 through the upper plate for applying samples to the gel. The geometry is similar to that of the X-box. The gel material between the plates is polyacrylamide or its equivalent. Such an apparatus is suitable for separating DNA molecules of up to 1,500 bases and thus allows more information to be obtained regarding DNA sequence than that from a standard sequencing gel.

We claim:

1. Gel electrophoresis apparatus for separating DNA molecules of high molecular weight comprising:
   means for generating a first electric field and a second electric field, said fields being oriented transversely to each other, and
   a gel box shaped and contoured to simultaneously form both said first and second fields into generally uniform electric fields, said gel box comprising a baffle means formed of electrically non-conducting material, said baffle means positioned and arranged to limit formation of a non-uniform electric field in said gel box.

2. The apparatus of claim 1, wherein said gel box comprises two non-conducting plates positioned to sandwich a gel therebetween.

3. The apparatus of claim 2, wherein said gel box comprises baffle means between said plates.

4. The apparatus of claim 1, 2 or 3 wherein said means comprises at least four electrodes.

5. The apparatus of claim 1, said baffle means being oriented along the overall direction of one electric field.

6. The apparatus of claim 5, said baffle means oriented along the overall direction of said first electric field and being positioned and arranged to limit formation of a non-uniform field in said second electric field.

7. The apparatus of claims 5 or 6, wherein said baffle means comprises a plurality of baffle elements.

8. The apparatus of claim 7, said plurality of baffle elements being oriented along the overall direction of said first electric field and arranged to constrain said second electric field to be generally uniform.

9. The apparatus of claim 1, said baffle means being in contact with the outer perimeter of said gel box.

10. The apparatus of claim 1, said baffle means being in contact with the base of said gel box.

11. The apparatus of claim 10, said baffle means having a height equal to that of said gel box.

12. The apparatus of claim 7, a said plurality of baffle elements being in contact with the outer perimeter of said gel box and extending along the overall direction of said first uniform electric field, to the edge of said second uniform electric field.

13. The apparatus of claim 1, 2 or 3 wherein said gel box has a wall defining the shape of said gel box and an outer perimeter of said gel box, said perimeter and a base together defining a volume for accepting a gel and buffer, said perimeter having the shape of two rectangles placed on top of each other at an angle of between 90°-135°.

14. The apparatus of claim 3, wherein said gel comprises polyacrylamide gel.

15. The apparatus of claim 4, wherein each said electrode is separated from other electrodes of the same polarity by a baffle element formed of electrically non-conducting material, said baffle element preventing direct electric conduction between electrodes of the same plurality through a medium positioned in said gel box.

16. The apparatus of claim 4 wherein said electrodes are positioned in the region of the outer perimeter of said box.

17. A method for separating DNA molecules of high molecular weight, comprising the steps of:

positioning said DNA molecules within a gel matrix,
providing means for generating alternating, transversely applied uniform electric fields,
positioning said gel matrix in a gel box shaped and contoured to simultaneously form two generally transverse uniform electric fields, said gel box comprising a baffle means formed of electrically nonconducting material, said baffle means positioned and arranged to limit formation of a non-uniform electric field in said gel box,
and subjecting said gel matrix to said alternating electric fields.

* * * * *

UNITED STATES PATENT AND TRADEMARK OFFICE
CERTIFICATE OF CORRECTION

PATENT NO. : 5,011,586
DATED : April 30, 1991
INVENTOR(S) : John D. Finney and Michael J. Finney It is certified that error appears in the above-identified patent and that said Letters Patent is hereby corrected as shown below:

Col. 5, line 34, "operator" should be --operation--.

Signed and Sealed this

Twenty-ninth Day of September, 1992

Attest:

DOUGLAS B. COMER

Attesting Officer     Acting Commissioner of Patents and Trademarks